US009333033B2

(12) United States Patent
Gliner

(10) Patent No.: US 9,333,033 B2
(45) Date of Patent: May 10, 2016

(54) DETECTION OF ABLATION ELECTRODE CONTACT WITH TISSUE

(71) Applicant: BIOSENSE WEBSTER (ISRAEL), LTD., Yokneam (IL)

(72) Inventor: Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 183 days.

(21) Appl. No.: 13/939,363

(22) Filed: Jul. 11, 2013

(65) Prior Publication Data

US 2015/0018813 A1 Jan. 15, 2015

(51) Int. Cl.

| | |
|---|---|
| ***A61B 18/12*** | (2006.01) |
| ***A61B 18/18*** | (2006.01) |
| *A61B 18/00* | (2006.01) |
| *A61B 19/00* | (2006.01) |

(52) U.S. Cl.

CPC ............ *A61B 18/18* (2013.01); *A61B 18/1233* (2013.01); *A61B 2018/00577* (2013.01); *A61B 2018/00642* (2013.01); *A61B 2018/00791* (2013.01); *A61B 2018/00886* (2013.01); *A61B 2018/00904* (2013.01); *A61B 2019/465* (2013.01); *A61B 2019/4836* (2013.01)

(58) Field of Classification Search

CPC .......... A61B 5/150954; A61B 1/6843; A61B 1/6844; A61B 2019/465; A61B 2018/00791–2018/00821; A61B 2018/00904

See application file for complete search history.

(56) References Cited

U.S. PATENT DOCUMENTS

| | | | | |
|---|---|---|---|---|
| 6,063,078 | A * | 5/2000 | Wittkampf | 606/41 |
| 8,206,380 | B2 | 6/2012 | Lenihan et al. | |
| 8,808,343 | B2 * | 8/2014 | Koch et al. | 607/96 |
| 2009/0312754 | A1 * | 12/2009 | Lenihan et al. | 606/33 |
| 2011/0295247 | A1 * | 12/2011 | Schlesinger et al. | 606/33 |
| 2012/0136348 | A1 | 5/2012 | Condie et al. | |
| 2013/0324993 | A1 * | 12/2013 | McCarthy et al. | 606/33 |

FOREIGN PATENT DOCUMENTS

| | | |
|---|---|---|
| WO | WO 98/40023 A1 | 9/1998 |

* cited by examiner

*Primary Examiner* — Ronald Hupczey, Jr.

(74) *Attorney, Agent, or Firm* — Louis J. Capezzuto

(57) ABSTRACT

A method includes delivering a Radio Frequency (RF) signal having a time-varying power from an intra-body probe to tissue in a vicinity of the probe in order to ablate the tissue. A temperature is measured in the vicinity of the probe. A decision is made as to whether the probe is in contact with the tissue, by comparing the measured temperature to a temperature threshold that varies in time depending on the time-varying power of the RF signal.

10 Claims, 3 Drawing Sheets

20
22
24
26
28
30
32
34
36
38
40
42
48

TEMP
(°C)
POWER
(W)
SAMPLE POINTS

DETECTION OF ABLATION ELECTRODE CONTACT WITH TISSUE

FIELD OF THE INVENTION

The present invention relates generally to invasive medical treatment, and specifically to detection of contact between a medical probe and tissue.

BACKGROUND OF THE INVENTION

Minimally-invasive intra-cardiac ablation is the treatment of choice for various types of arrhythmias. To perform such treatment, the physician typically inserts a catheter through the vascular system into the heart, brings the distal end of the catheter into contact with myocardial tissue in areas of abnormal electrical activity, and then energizes one or more electrodes at or near the distal end in order to create tissue necrosis.

A number of systems for intra-cardiac ablation therapy are commercially available, such as the CARTO™ system offered by Biosense Webster Inc. (Diamond Bar, Calif.). CARTO tracks the position and operating parameters of the distal end of the catheter and displays this information electronically on a three-dimensional (3D) anatomical map of the heart.

U.S. Pat. No. 8,206,380, whose disclosure is incorporated herein by reference, describes a method for measuring the contact force exerted on tissue by a probe for heating the tissue and containing an antenna which is connected to a radiometer whose output reading indicates the temperature at depth of the tissue contacted by the probe. The method comprises displaying the output reading of the radiometer, applying sufficient power to the probe to heat the tissue to a selected first temperature that is not lethal to the tissue, moving the probe into contact with the tissue, observing the increase in the displayed temperature reading that occurs when the probe contacts the tissue, and advancing the probe toward the tissue until the displayed temperature reading reaches a value corresponding to a selected tissue contact force. After the probe position in the tissue has stabilized, the applied power to the probe may be increased to heat the tissue to a selected second temperature that is lethal to tissue for a sufficient time to ablate the tissue followed by lowering the tissue heating to a sub-lethal temperature.

U.S. Patent Application Publication 2012/0136348, whose disclosure is incorporated herein by reference, describes a medical method, device, and system, including advancing an ablation element of a medical device into contact with tissue to be treated, selecting a power level of energy to ablate the tissue, delivering energy at the selected power level to the ablation element, determining whether the ablation element is in continuous contact with the tissue, and reducing the selected power level when the ablation element ceases to be in continuous contact with the tissue.

PCT International Publication WO/9840023, whose disclosure is incorporated herein by reference, describes a system for ablating tissue within a body, the system having: an energy source providing a level of energy which is not damaging to the cellular structures of the body tissue, a catheter coupled to the energy source, the catheter having an electrode; and means for sensing the temperature of the electrode while also sensing the amount of energy which is not damaging to the cellular structures of the body tissue is delivered to the electrode, the sensing means coupled to the catheter and coupled to the energy source wherein the degree to which the electrode contacts the heart tissue (e.g. no contact, moderate contact, good contact or excellent contact) may be determined.

SUMMARY OF THE INVENTION

An embodiment of the present invention described herein provides a method including delivering a Radio Frequency (RF) signal having a time-varying power from an intra-body probe to tissue in a vicinity of the probe in order to ablate the tissue. A temperature is measured in the vicinity of the probe. A decision is made as to whether the probe is in contact with the tissue, by comparing the measured temperature to a temperature threshold that varies in time depending on the time-varying power of the RF signal.

In some embodiments, comparing the measured temperature to the temperature threshold includes setting the temperature threshold depending on a fourth root of the power of the RF signal. In other embodiments, the method includes setting a proportion coefficient between the measured temperature and the fourth root of the power of the RF signal, based on a first coefficient that links the measured temperature and the fourth root of the power when the probe is in contact with the tissue, and a second coefficient that links the measured temperature and the fourth root of the power when the probe is not in contact with the tissue.

In some embodiments, setting the proportion coefficient includes assigning the proportion coefficient to be an average of the first and second coefficients. In other embodiments, the method includes outputting an indication of whether the probe is in contact with the tissue to an operator. In yet other embodiments, deciding whether the probe is in contact with the tissue includes comparing the measured temperature to the temperature threshold only when the power of the RF signal is above a predefined level.

There is additionally provided herein, in accordance with an embodiment of the present invention, an apparatus including a signal generator and a processor. The signal generator is configured to deliver a Radio Frequency (RF) signal having a time-varying power to an intra-body probe, for application to tissue in a vicinity of the probe, in order to ablate the tissue. The processor is configured to receive a measurement of a temperature in the vicinity of the probe, and to decide whether the probe is in contact with the tissue by comparing the measured temperature to a temperature threshold that varies in time depending on the time-varying power of the RF signal.

There is additionally provided herein, in accordance with an embodiment of the present invention, a computer software product, including a non-transitory computer-readable medium in which program instructions are stored, which instructions, when read by a processor in an ablation system that delivers a Radio Frequency (RF) signal having a time-varying power from an intra-body probe to tissue in order to ablate the tissue, cause the processor to measure a temperature in the vicinity of the probe, and to decide whether the probe is in contact with the tissue by comparing the measured temperature to a temperature threshold that varies in time depending on the time-varying power of the RF signal.

There is additionally provided herein, in accordance with an embodiment of the present invention, an apparatus including a processor and an interface for communicating with an ablation system that delivers a Radio Frequency (RF) signal having a time-varying power from an intra-body probe to tissue in a vicinity of the probe in order to ablate the tissue. The processor is configured to receive a measurement of a temperature in the vicinity of the probe, and to decide whether the probe is in contact with the tissue by comparing the measured temperature to a temperature threshold that varies in time depending on the time-varying power of the RF signal.

The present invention will be more fully understood from the following detailed description of the embodiments thereof, taken together with the drawings in which:

DETAILED DESCRIPTION OF EMBODIMENTS

Overview

In a radio-frequency (RF) ablation procedure, an intra-body probe is navigated through the patient's body into an organ or cavity. The distal end of the probe comprises an ablation electrode through which RF energy is applied to tissue contacting the probe, inducing local necrosis of the tissue. In order to perform ablation properly, it is important to verify that the probe is indeed in physical contact with the tissue.

Embodiments of the present invention that are described herein provide methods and systems for verifying whether the ablation probe is in contact with the tissue. In the disclosed techniques, a processor measures the temperature at the distal tip of the probe, and compares the measured temperature to a threshold temperature. If the measured temperature exceeds the threshold temperature, the processor decides that the probe is in physical contact with the tissue. If the measured temperature is below the threshold temperature, the processor decides that there is no physical contact. The processor outputs a "contact/no-contact" indication to the operator of the procedure.

In the disclosed embodiments, the threshold temperature depends on the power level of the applied ablation signal. As such, the threshold temperature varies with time, typically increasing as the ablation power increases along the procedure. In an example embodiment, the measured temperature can be modeled as proportional to the fourth root of the ablation power, in accordance with the Stefan-Boltzmann law. In this model, the proportion coefficient differs depending on whether the probe is in contact with the tissue or not. In this embodiment, the threshold temperature is set between the two possible modeled temperatures (assuming contact and assuming no contact).

System Description

Figure 1:
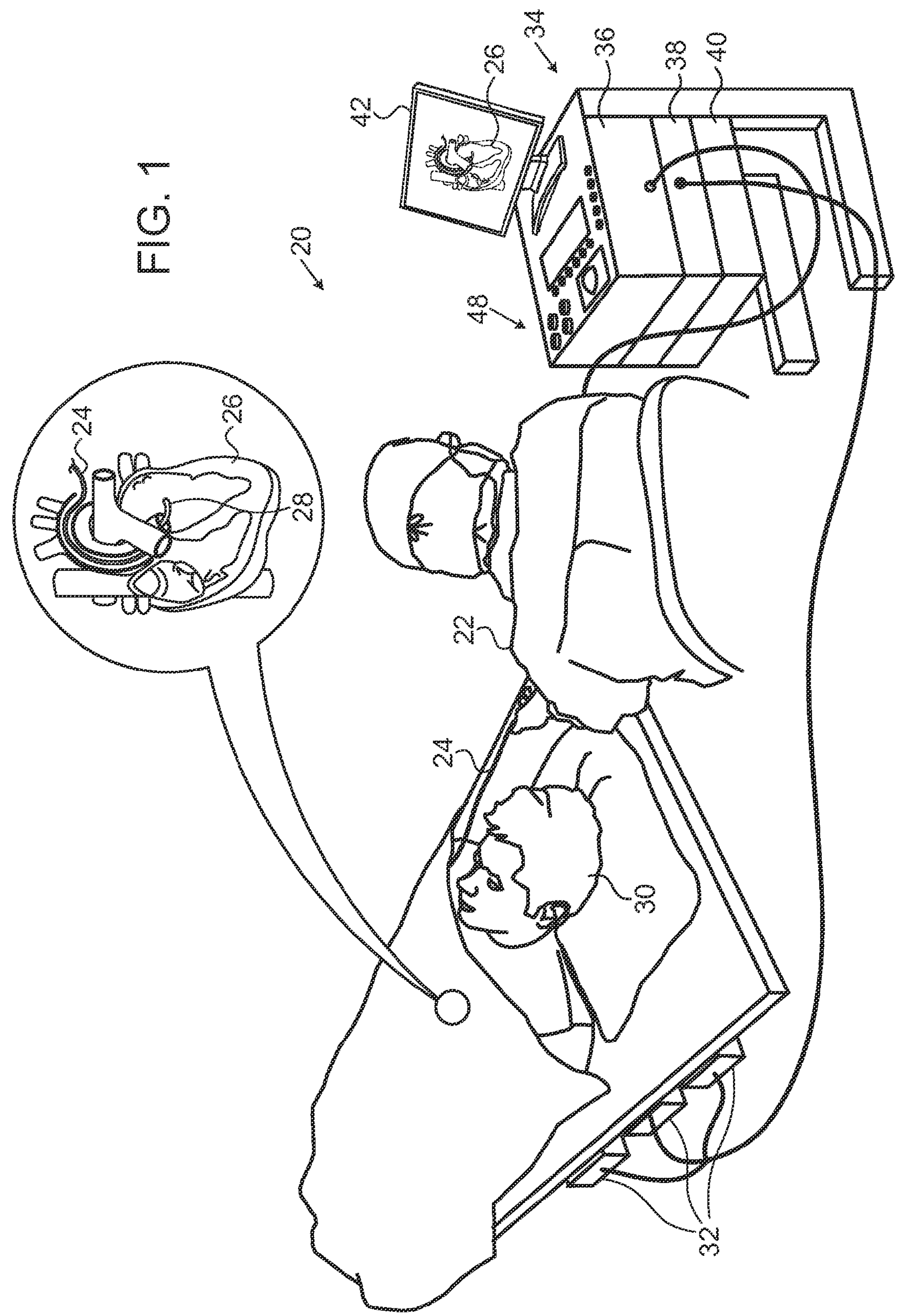
FIG. 1 is a schematic, pictorial illustration of a cardiac mapping and ablation system, which operates in accordance with an embodiment of the invention.

FIG. 1 is a schematic, pictorial illustration of a cardiac mapping and ablation system 20, which operates in accordance with an embodiment of the invention. System 20 may be based, for example, on the above-mentioned CARTO system, with suitable additions to the system software. System 20 comprises an intra-body probe, such as a catheter 24, and a control console 34. Typically, catheter 24 is used in ablating sites of arrhythmias in one or more chambers of a heart 26 of a patient 30. Further alternatively, catheter 24 or other suitable probes may be used for other therapeutic purposes in the heart or in other body organs.

An operator 22, such as a cardiologist, inserts catheter 24 through the vascular system of patient 30 so that the distal end of the catheter enters a chamber of heart 26. Operator 22 advances the catheter so that an electrode 28 at the distal end of the catheter contacts endocardial tissue at desired ablation sites. Catheter 24 is typically connected by a suitable connector at its proximal end to console 34, and specifically to a radio frequency (RF) generator 36, which generates RF energy for transmission via catheter 24 to electrode 28. Operator 22 actuates RF generator 36 to ablate tissue at suspected sites of arrhythmia in the heart.

A temperature sensor (not shown), such as a thermocouple, near the distal end of catheter 24 measures the temperature at the distal end. A signal processor 40 in console 34 processes the thermocouple electrical signals and is configured to determine if the distal end is in contact with the tissue using the embodiments taught herein as will be described later.

Processor 40 may also be configured to perform other functions, such as catheter tracking within the cavity of the body. In an example embodiment, System 20 comprises magnetic field generators 32 that are driven by a signal source 38. Processor 40 receives tracking signals from magnetic position sensors fitted in the distal end of catheter 24, such as used in the CARTO System as previously cited.

In some embodiments, catheter 24 may be configured with holes near the distal end to allow a flow of irrigation solution, such as saline solution, for example, to cool the tissue-electrode interface after applying the RF signal during the ablation procedure.

Processor 40 in console 34 typically comprises a general-purpose computer processor, with suitable front end and interface circuits for receiving signals from catheter 24 and for controlling and receiving inputs from the other components of console 34. Processor 40 may be programmed in software to carry out the functions that are described herein. The software may be downloaded to processor 40 in electronic form, over a network, for example, or it may be provided, alternatively or additionally, on tangible, non-transitory media, such as optical, magnetic or electronic memory media. Further alternatively or additionally, some or all of the functions of processor 40 may be carried out by dedicated or programmable digital hardware components.

Based on the signals received from catheter 24 and other components of system 20, processor 40 drives a display 42 to present operator 22 with a three-dimensional (3D) map 44 of heart 26 and an indication of whether the catheter is contacting the heart tissue during ablation. The contact status indication may be shown to the operator directly on map 44, a text that appears on display 42, or by any other suitable method to notify the operator of the ablation electrode contact status. Other parameters that may be measured by catheter 24 and by other elements of system 20 and shown on display 42 may include, for example, electrical impedance of the heart tissue, local temperature, and RF power delivered through the catheter.

Detecting Ablation Electrode Contact with Tissue

In embodiments of the present invention, catheter 24 measures the temperature of its distal tip using a temperature sensor (not shown) near ablation electrode 28. Processor 40 compares the measured temperature to a threshold temperature, which depends on the applied RF power to ablation electrode 28 to be described below. Processor 40 then determines if ablation electrode 28 is in physical contact with the tissue based on the comparison.

For example, if the processor 40 assesses that the measured temperature is above the threshold temperature, then processor 40 sends an indication to operator 22 that ablation electrode 28 is contacting the tissue during the procedure, and vice versa. (The terms "threshold temperature" and "temperature threshold" are used interchangeably herein.)

When RF power is applied to ablation electrode 28, the temperature rise at the probe-tissue interface depends, for example, on the thermal properties and geometry of fluids and tissue surrounding electrode 28. The temperature rise is affected by the thermal properties of the tissue being ablated, blood in the region of the tissue and electrode 28, and any irrigation solution applied to the electrode-tissue interface. The environment at the electrode-tissue interface is different when ablation electrode 28 is contacting the tissue, or not contacting the tissue.

The input power P to ablation electrode 28 in watts is a known metric during the therapeutic procedure. P is approximately the power radiated by ablation electrode 28, which is related to the absolute temperature T of the electrode-tissue interface through the Stefan-Boltzmann equation. When ablation electrode 28 contacts the tissue, the Stefan-Boltzmann equation is given by:

$$P=A_c \cdot T^4 \quad (1)$$

Similarly, when ablation electrode 28 is not contacting the tissue, the Stefan-Boltzmann equation is given by:

$$P=A_{NC} \cdot T^4 \quad (2)$$

$A_C$ and $A_{NC}$ in equations (1) and (2) are constants that depend on the Stefan's constant as well as on an effective area of the electrode-tissue interface and the emissivity of the electrode $\epsilon$. $A_C$ denotes the constant that links the power and temperature when the probe is assumed to be in contact with the tissue, and $A_{NC}$ denotes the constant that links the power and temperature when there is no contact.

The temperature at the electrode-tissue interface can be measured by temperature sensors placed at the distal end of catheter 24. In some embodiments, the temperature sensor comprises one or more thermocouples incorporated into the ablation electrode such that temperature T is an average of the electrical outputs from the one or more thermocouples.

Equations (1) and (2) may be rewritten as:

$$T = a_C \cdot P^{\frac{1}{4}} \quad (3)$$

$$T = a_{NC} \cdot P^{\frac{1}{4}} \quad (4)$$

wherein $a_C$ and $a_{NC}$ denote proportion coefficients between the measured temperature T and the fourth root of the ablation power P in the contact and non-contact scenarios, respectively. Proportion coefficients $a_C$ and $a_{NC}$ are the reciprocal values of $A_C$ and $A_{NC}$ from equations (1) and (2), respectively.

Although the Stefan-Boltzmann equation relates to a perfect black-body radiator, the tissue typically behaves as a "grey body" (e.g., not as a perfect black-body), whose measured temperature T is still proportional to $P^{1/4}$ as for black-body radiation, but with grey body proportionality coefficients (in the present case $a_C$ and $a_{NC}$). The values of coefficients $a_C$ and $a_{NC}$ can be computed or estimated by experimentation, e.g., during respective measurements of P and T for known contact and non-contact scenarios. Alternatively, the values of coefficients $a_C$ and $a_{NC}$ can be computed by simulation, by analytical or numerical modeling, or in any other suitable way.

The embodiments of the present invention described herein utilize the difference between the contact and non-contact coefficients $a_C$ and $a_{NC}$ to determine if ablation electrode 28 contacts the tissue. In these embodiments, processor 40 computes a threshold temperature based on the applied RF power and the two coefficients.

In some embodiments, the threshold temperature $T_{th}$ is derived from an average of the two coefficients and given by:

$$T_{th} = \left(\frac{a_C + a_{NC}}{2}\right) \cdot P^{\frac{1}{4}} + b \quad (5)$$

wherein b is an offset term that can be determined by experimentation, simulation or analytical or numerical modeling. In alternative embodiments, the threshold temperature may be calculated in any other suitable way based on the two coefficients.

Typically, the ablation power P varies with time during the procedure. In a typical ablation procedure, physician 22 gradually increases the ablation power until reaching the desired result or until reaching some safety limitation. In some cases the ablation power may be reduced, e.g., in order to avoid damage. Since P is time-varying and $T_{th}$ depends on P, the threshold temperature $T_{th}$ is time varying and changes along the ablation procedure.

Figure 2:
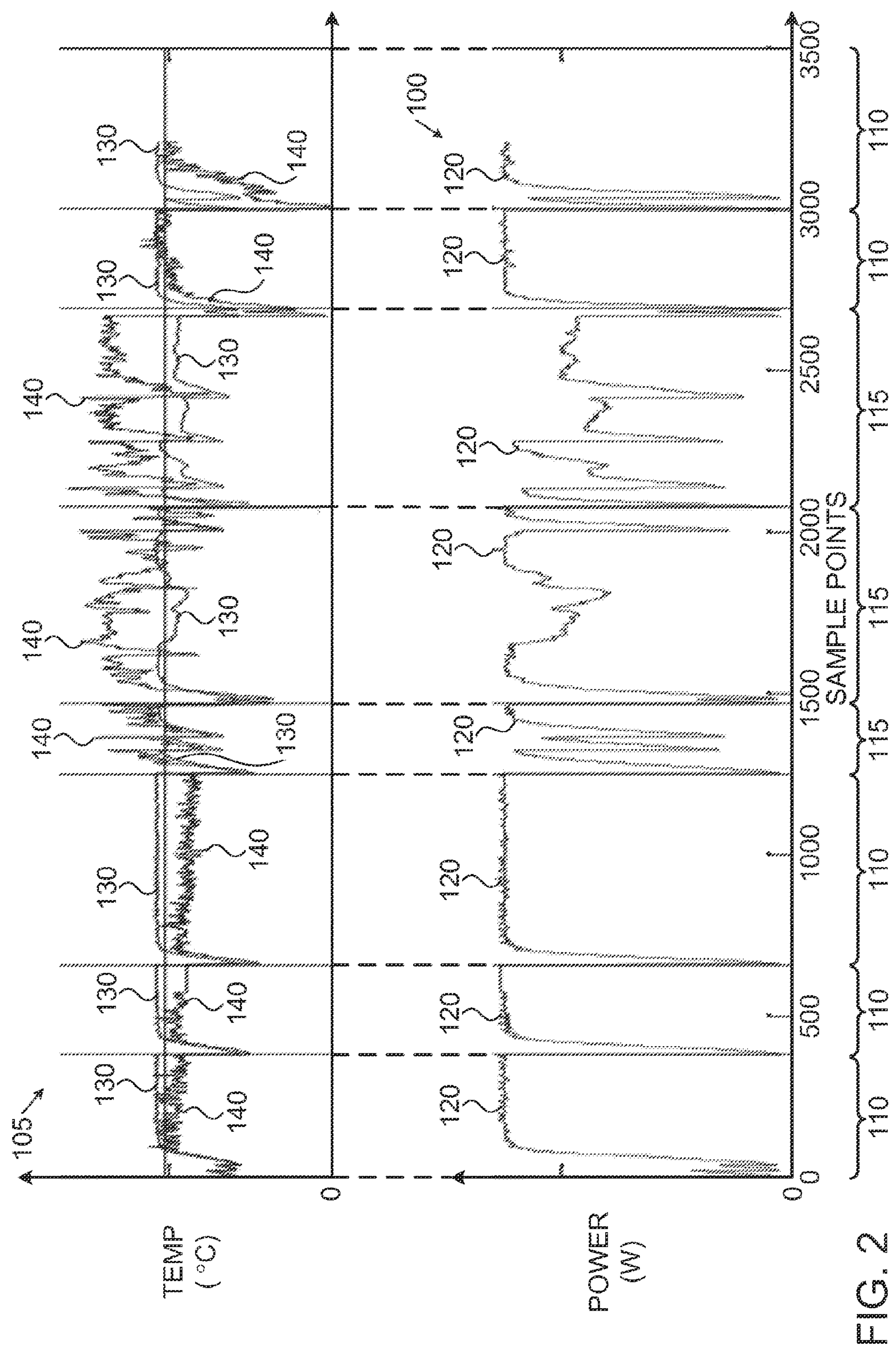
FIG. 2 is a diagram that schematically illustrates signal waveforms used in determining ablation electrode tissue contact, in accordance with an embodiment of the present invention.

FIG. 2 is a diagram that schematically illustrates signal waveforms used in determining tissue contact with ablation electrode 28, in accordance with an embodiment of the present invention. The graph describes eight example ablation procedures. Intervals 110 illustrate ablation procedures in which electrode 28 is not in contact with the tissue when RF ablation power is applied. Intervals 115 illustrate ablation procedures in which electrode 28 is in physical contact with the tissue during ablation.

The bottom graph in FIG. 2 shows a time varying waveform 120 of RF power P applied to ablation electrode 28 as a function of data sample points over time acquired by processor 40. The top graph of FIG. 2 shows a plot of the measured catheter tip temperature as a function of data sample points over time acquired by processor 40. A tip temperature waveform 140 measured over time by the temperature sensor is plotted on the same horizontal scale as the lower graph. A waveform 130 shows the corresponding values of the threshold temperature $T_{th}$. As can be seen in the figure, the threshold temperature (waveform 130) is time-varying and tracks the ablation power level (waveform 120).

The threshold temperature in this example is derived from equation (5) which may be rewritten as:

$$T_{th} = a \cdot P^{\frac{1}{4}} + b \quad (6)$$

wherein a denotes the average between $a_C$ and $a_{NC}$. In the example of FIG. 2, a=6.7 and b=26, such that equation (6) can be rewritten as $$T_{th} = 6.7 \cdot P^{\frac{1}{4}} + 26 \quad (7)$$

The time varying threshold temperature waveform 130 shown in FIG. 2 is computed using equation (7) with applied RF power waveform 120.

As can be seen in the figure, when the ablation electrode is not in contact with the tissue (in intervals 110), measured temperature waveform 140 is below threshold temperature waveform 130. When the ablation electrode is in contact with the tissue (in intervals 115), threshold temperature waveform 130 is above measured temperature waveform 140. This example demonstrates the effectiveness of the threshold mechanism described herein.

In the embodiments of the present invention, processor 40 uses the differences between the measured and threshold temperatures shown in FIG. 2 to assess whether ablation electrode 28 contacts the tissue during the therapeutic procedure. When waveform 140 is greater than waveform 130 in any given time interval (e.g., in a given slice of sample points shown in FIG. 2), processor 40 concludes that the ablation probe is in contact with the tissue, and vice versa.

In some embodiments, processor 40 uses the above-described threshold mechanism only when the ablation power is above some predefined value, e.g., 5 watts. It has been found by the inventors that this technique works well, for example, with probes that are configured to apply irrigation to cool the ablated tissue.

In some embodiments, an algorithm based on Equation (6) that may be used by system 20 for this case is given by:

```
If (P>Minimal_power) {
    If ( (A_thresh* (P) ^ (1/4) +B_thresh<T)
    Contact=1;
    Else
    Contact=0;
}
```

The algorithm assesses that when P is greater than the predefined threshold power (e.g., 5 watts) and P is greater than the threshold temperature as in equation (6), the probe is in contact with the tissue (e.g., contact=1 in the algorithm).

Figure 3:
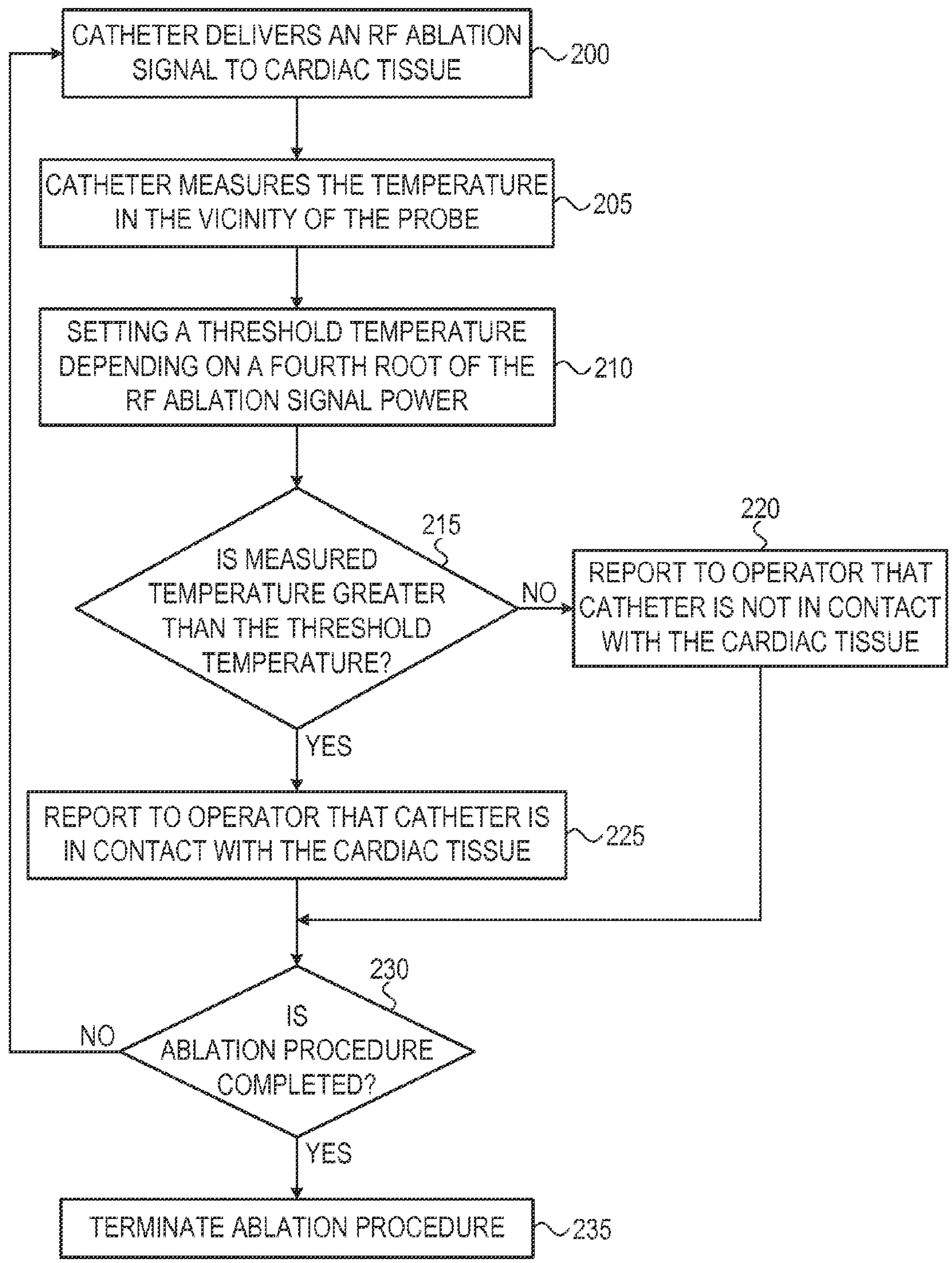
FIG. 3 is a flow chart that schematically illustrates a method for determining ablation electrode tissue contact, in accordance with an embodiment of the present invention.

FIG. 3 is a flow chart that schematically illustrates a method for determining ablation electrode tissue contact, in accordance with an embodiment of the present invention. In a delivering step 200, catheter 24 delivers an RF ablation signal to cardiac tissue. The RF ablation signal is produced by generator 36, and its power level typically varies with time. In a measuring step 205, catheter 24 measures the temperature in the vicinity of the catheter tip, typically using a temperature sensor near the tip. In a setting step 210, processor 40 sets a threshold temperature depending on a fourth root of the RF ablation signal power as shown in equations (5) and (6).

In a first decision step 215, processor 40 assesses if the measured temperature is greater than the threshold temperature. If not, in a first reporting step 220, processor 40 reports to operator 22 that the catheter is not in contact with the cardiac tissue. If so, in a second reporting step 225, processor 40 reports to operator 22 that the catheter is in contact with the cardiac tissue.

System 20 can indicate the presence or absence of catheter-tissue contact in various ways, such as using a suitable visual indication on display 42. In a second decision step 230, processor 40 assesses if the ablation procedure is completed. If not, ablation continues with delivering step 200. If so, the ablation procedure is terminated in a terminating step 235.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:

delivering a Radio Frequency (RF) signal having a time-varying power from an intra-body probe to tissue in a vicinity of the probe in order to ablate the tissue;

measuring a temperature in the vicinity of the probe; and deciding whether the probe is in contact with the tissue by comparing the measured temperature to a temperature threshold that varies in time depending on the time-varying power of the RF signal by setting the temperature threshold depending on a fourth root of the power of the RF signal and setting a proportion coefficient between the measured temperature and the fourth root of the power of the RF signal, based on a first coefficient that links the measured temperature and the fourth root of the power when the probe is in contact with the tissue, and a second coefficient that links the measured temperature and the fourth root of the power when the probe is not in contact with the tissue.

2. The method according to claim 1, wherein setting the proportion coefficient comprises assigning the proportion coefficient to be an average of the first and second coefficients.

3. The method according to claim 1, and further comprising outputting an indication of whether the probe is in contact with the tissue to an operator.

4. The method according to claim 1, wherein deciding whether the probe is in contact with the tissue comprises comparing the measured temperature to the temperature threshold only when the power of the RF signal is above a predefined level.

5. Apparatus, comprising:

a signal generator, which is configured to deliver a Radio Frequency (RF) signal having a time-varying power to an intra-body probe, for application to tissue in a vicinity of the probe, in order to ablate the tissue; and a processor, which is configured to receive a measurement of a temperature in the vicinity of the probe, and to decide whether the probe is in contact with the tissue by comparing the measured temperature to a temperature threshold that varies in time depending on the time-varying power of the RF signal, and wherein the processor is configured to set the temperature threshold depending on a fourth root of the power of the RF signal and to set a proportion coefficient between the measured temperature and the fourth root of the power of the RF signal, based on a first coefficient that links the measured temperature and the fourth root of the power when the probe is in contact with the tissue, and a second coefficient that links the measured temperature and the fourth root of the power when the probe is not in contact with the tissue.

6. The apparatus according to claim 5, wherein the processor is configured to set the proportion coefficient to an average of the first and second coefficients.

7. The apparatus according to claim 5, wherein the processor is configured to output an indication of whether the probe is in contact with the tissue to an operator.

8. The apparatus according to claim 5, wherein the processor is configured to compare the measured temperature to the temperature threshold only when the power of the RF signal is above a predefined level.

9. A computer software product, comprising a non-transitory computer-readable medium in which program instructions are stored, which instructions, when read by a processor in an ablation system that delivers a Radio Frequency (RF) signal having a time-varying power from an intra-body probe to tissue in order to ablate the tissue, cause the processor to measure a temperature in the vicinity of the probe, and to decide whether the probe is in contact with the tissue by comparing the measured temperature to a temperature threshold that varies in time depending on the time-varying power of the RF signal by setting the temperature threshold depending on a fourth root of the power of the RF signal and setting a proportion coefficient between the measured temperature and the fourth root of the power of the RF signal, based on a first coefficient that links the measured temperature and the fourth root of the power when the probe is in contact with the tissue, and a second coefficient that links the measured temperature and the fourth root of the power when the probe is not in contact with the tissue.

10. Apparatus, comprising:

an interface for communicating with an ablation system that delivers a Radio Frequency (RF) signal having a time-varying power from an intra-body probe to tissue in a vicinity of the probe in order to ablate the tissue; and a processor, which is configured to receive a measurement of a temperature in the vicinity of the probe, and to decide whether the probe is in contact with the tissue by comparing the measured temperature to a temperature threshold that varies in time depending on the time-varying power of the RF signal by setting the temperature threshold depending on a fourth root of the power of the RF signal and setting a proportion coefficient between the measured temperature and the fourth root of the power of the RF signal, based on a first coefficient that links the measured temperature and the fourth root of the power when the probe is in contact with the tissue, and a second coefficient that links the measured temperature and the fourth root of the power when the probe is not in contact with the tissue.

* * * * *